US006916941B2

(12) United States Patent
Christensen et al.

(10) Patent No.: US 6,916,941 B2
(45) Date of Patent: Jul. 12, 2005

(54) CRYSTALLINE COMPOSITION CONTAINING ESCITALOPRAM

(75) Inventors: Troels Volsgaard Christensen, Holbæk (DK); Ken Liljegren, Værløse (DK); Michiel Onne Elema, København Ø (DK); Lene Andresen, Rødovre (DK); Shashank Mahashabde, Kendall Park, NJ (US); Sebastian P. Assenza, Fort Salonga, NY (US)

(73) Assignee: H. Lundbeck A/S, Valby-Copenhagen (DK)

( * ) Notice: Subject to any disclaimer, the term of this patent is extended or adjusted under 35 U.S.C. 154(b) by 18 days.

(21) Appl. No.: 10/403,453

(22) Filed: Mar. 31, 2003

(65) Prior Publication Data

US 2003/0212128 A1 Nov. 13, 2003

Related U.S. Application Data

(63) Continuation of application No. PCT/DK02/00513, filed on Jul. 25, 2002.

(30) Foreign Application Priority Data

Jul. 31, 2001 (DK) .................................. PA 2001 01164

(51) Int. Cl.$^7$ .................... C07D 307/78; C07D 307/87; A61K 31/343
(52) U.S. Cl. ........................ 549/467; 549/469; 514/469
(58) Field of Search ............................... 549/467, 469; 514/469

(56) References Cited

U.S. PATENT DOCUMENTS

| | | |
|---|---|---|
| 3,467,675 A | 9/1969 | Petersen et al. |
| 4,136,193 A | 1/1979 | Bogeso et al. |
| 4,650,884 A | 3/1987 | Bogeso |
| 4,721,723 A | 1/1988 | Barnes et al. |
| 4,943,590 A | 7/1990 | Boegesoe et al. |
| 5,296,507 A | 3/1994 | Tanaka et al. |
| 5,683,720 A | 11/1997 | Myers et al. |
| 5,840,334 A | 11/1998 | Raiden et al. |
| 5,869,098 A | 2/1999 | Misra et al. |
| 5,980,941 A | 11/1999 | Raiden et al. |
| 2001/0049450 A1 | 12/2001 | Ikemoto et al. |

FOREIGN PATENT DOCUMENTS

| | | |
|---|---|---|
| CA | 2178637 | 6/1995 |
| CA | 2163840 | 5/1996 |
| CA | 2291067 | 5/1998 |
| CA | 2291072 | 5/1998 |
| CA | 2291129 | 6/1999 |
| CA | 2291134 | 4/2000 |
| EP | 0 171 943 A1 | 11/1988 |
| EP | 0 347 066 A1 | 12/1989 |
| EP | 0 714 663 A2 | 6/1996 |
| EP | 07140663 A3 | 1/1997 |
| EP | 1 152 000 A1 | 11/2001 |
| GB | 1358915 | 7/1974 |
| GB | 2357762 | 7/2001 |
| WO | WO-99/03469 | 1/1999 |
| WO | WO 00/11926 A2 | 3/2000 |
| WO | WO 01/22941 A1 | 4/2001 |
| WO | WO-01/68627 | 9/2001 |

OTHER PUBLICATIONS

International Search Report for PCT/DK02/00513, 2002.
Kirk–Othmer, *Encyclopedia of Chemical Technology*, Second Edition, vol. 6:482, New York, John Wiley & Sons, 1965.
Kunsemuller, Johannes, Ed., *Meyers Lexikon der Technik und der exakten Naturwissenschaften*: 1151, Mannheim/Wien/Zurich: Bibliographisches Institute (1970).
Bates, Robert B., et al., Ed. *Research Techniques in Organic Chemistry*: 50–52, Englewood Cliffs, NJ: Prentice Hall, Inc. (1971).
*Organikum: Organisch–Chemisches Grundpraktikum*: pp. 39–41, Veb Deutscher Verlag Der Wissenschaften, Berlin (1974).
Hyttel, John, "Citalopram—Pharmacological Profile of a Specific Serotonin Uptake Inhibitor with Antidepressant Activity,"*Prog. Neuro–Psychopharmacol & Biol. Psychiat.* 6: 277–295 (1982).
Gravem, A., et al. "A double–blind comparison of citalopram (Lu 10–171) and amitriptyline in depressed patients," *Acta Psychiatr. Scand.* 75: 478–486 (1987).
Furniss, Brian, Ed., *Vogel's Textbook of Practical Organic Chemistry*, Fifth Edition: 135–6, New York: Longman Scientific & Technical (john Wiley & Sons, Inc.) (1989).
Numberg, E., et al., Ed., *Hagers Handbuch der pharmazeutishen Praxis*, vol. 5: 549–51, Springer–Verlag: Wissenschaftlicher Beirat (1991).
Kirk–Othmer, *Encyclopedia of Chemical Technology*, Fourth Edition, vol. 7: 683–5, New York: John Wiley & Sons (1993).
Webpage from Lundbeck website (www.lundbeck.com), company's activities Sep. 26, 2003.
Webpage from Lundbeck website (www.lundbeck.com): Product information on Cipramll Sep. 26, 2003.
Remington's Pharmaceutical Sciences, 18th Edition, Chapter 89, Oral Solid Dosage Forms pp. 1633–1658, 1990.
Bhogi B. Sheth, et al., Compressed Tablets, Chapter 3 in Pharmaceutical Dosage Forms: Tablets, vol. 1, H. Lieberman and L. Lachman eds., Marcel Dekker, Inc., New York and Basel, 1979, pp. 109–185.

(Continued)

Primary Examiner—Ba K. Trinh
(74) Attorney, Agent, or Firm—Darby & Darby

(57) ABSTRACT

Crystalline particles of escitalopram oxalate with a particle size of at least 40 μm is disclosed. Method for the manufacture of said crystalline particles and pharmaceutical compositions comprising said crystalline particles are also disclosed.

47 Claims, No Drawings

OTHER PUBLICATIONS

Chapters 2 to 4 in Pharmaceutical Dosage Forms: Tablets, vol. 1, H. Lieberman and L. Lachman, eds., Marcel Dekker, Inc. New York and Basel 1989, pp. 75–246 (Chapter 2: Tablet and Formulation Design; Chapter 3: Compressed Tablets by Wet Granulation; Chapter 4: Compressed Tablets by Direct Compression).

Keith Marshall, Compression and Consolidation of Powdered Solids, Chapter 4, The Theory and Practise of Industrial Pharmacy, Lieberman, Lachman, and Kanig, eds., 3rd Edition, 1986, pp. 66–99.

Hoener et al., Chapter 4, Factors Influencing Drug Absorption and Drug Availability, Modern Pharmaceutics, 3rd edition, Banker and Rhodes, eds., Marcel Dekker, New York and Basel, 1995, pp. 121–153.

Edward M. Rudnic, et al., Chapter 10, Tablet Dosage Forms, Modern Pharmaceutics, 3d edition, Banker and Rhodes, eds., Marcel dekker, New York and Basel, 1995, pp. 333–394.

Joseph B. Schwartz, et al., Chapter 18, Optimazation Techniques in Pharmaceutical Formulation and Processing, Modern Pharmaceutics, 3rd Edition, Banker and Rhodes, eds., Marcel Dekker, New York and Basel, 1995, pp. 727–752.

Gunsel, et al, Chapter 11, Tablets, The Theory and Practice of Industrial Pharmacy Lieberman, Lachman, and Kanig, eds., 2nd edition, 1976, pp. 321–358.

Keith Marshall, Chapter 10, Solid Oral Disage Forms, Modern Pharmaceutics, 1st Edition, Banker and Rhodes, eds., Marcel Dekker, New York and Basel, 1979, p. 359–427.

Vogel's Textbook of Practical Organic Chemistry, Fourth Edition, pp. 100–263, 1978.

Dr. Fritz Gstimer, Professor fur Pharmazeutische Technologie an der Universitat Bonn, 1973, Einfuhrung in Die Verfahrenstechnik Der Arzneiformung, pp. 201–203 (and English Translation).

O'Connor, R.E. et al., Chapter 91 Powders, Remington: The Science and Practise of Pharmacy, 19th Ed., A. Gennaro, editor, Mack Publishing Co., Easton, 1995, pp. 1598–1613.

Banker, G.S., et al., Chapter 11, Tablets, The Theory and Practice of Industrial Pharmacy, Lieberman, Lachman, and Kanig, eds, 3rd Edition, 1988, pp. 293–345.

Hoener et al., Chapter 4, Factors Influencing Drug Absorption and Drug Availability, Modern Pharmaceutics, 1st edition, Banker and Rhodes, eds., Marcel Dekker, New York and Basel, 1979, pp. 143–182.

Joseph B. Schwartz, et al., Chapter 17, Optimization Techniques in Pharmaceutical Formulation and Processing, Modern Pharmaceutics, 1st Edition, Banker and Rhodes, eds., Marcel Dekker, New York and Basel, 1979, pp. 711–734.

N. Hirayama "Crystallization by control of temperature change," from "Handbook for Preparing Organic Crystals," SECTION 3/1/1, pp. 34–35 (Apr. 20, 2000) (and English language translation).

Pierre Carre, "Dissolution dans les Liquides," Precis de Technologie et de Chimie Industrielle: 319–320, Librairie J.–B. Bailliere et Fils (1938) (and English language translation).

CRYSTALLINE COMPOSITION CONTAINING ESCITALOPRAM

This application is a continuation of International Application No. PCT/DK02/00513 filed Jul. 25, 2002. The prior application is hereby incorporated by reference in its entirety.

The present invention relates to crystalline preparations of the oxalate salt of the compound escitalopram (INN-name), which is the S-enantiomer of the well-known antidepressant drug citalopram, i.e. (S)-1-[3-(dimethylamino)propyl]-1-(4-fluorophenyl)-1,3-dihydro-5-isobenzofurancarbonitrile oxalate.

BACKGROUND OF THE INVENTION

Citalopram is a well-known antidepressant drug that has the following structure:

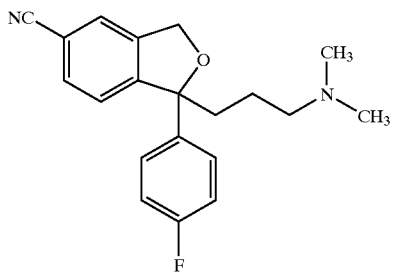

It is a selective, centrally active serotonin (5-hydroxytryptamine; 5-HT) reuptake inhibitor, accordingly having antidepressant activities.

Citalopram was first disclosed in DE 2,657,013, corresponding to U.S. Pat. No. 4,136,193. This patent publication describes the preparation of citalopram by one method and outlines a further method, which may be used for preparing citalopram. The citalopram prepared was isolated in crystalline form as the oxalate, the hydrobromide and the hydrochloride salt, respectively. Furthermore, the citalopram base was obtained as an oil (B.P. 175° C./0.03 mmHg). The publication also outlines the manufacture of tablets containing salts of citalopram. Citalopram is marketed as the hydrobromide and the hydrochloride, respectively.

Escitalopram, the pharmaceutical activity thereof and crystalline escitalopram oxalate are disclosed in U.S. Pat. No. 4,943,590. Methods for preparation of pharmaceutical preparations of escitalopram are outlined.

Citalopram is marketed in a number of countries as a tablet prepared by compression of granulated citalopram hydrobromide, lactose and other excipients. It is well recognised that preparation of tablets with a reproducible composition requires that all the dry ingredients have good flow properties. In cases, where the active ingredient has good flow properties, tablets can be prepared by direct compression of the ingredients. However, in many cases the particle size of the active substance is small, the active substance is cohesive or has poor flow properties.

Further, active substances with a small particle size mixed with excipients having a larger particle size will typically segregate or de-mix during the tabletting process. The problem of small particle size and poor flowability is conventionally solved by enlarging the particle size of the active substance, usually by granulation of the active ingredient either alone or in combination with a filler and/or other conventional tablet ingredients.

One such granulation method is the "wet" granulation process. Using this method, the dry solids (active ingredients, filler, binder etc.) are blended and moistened with water or another wetting agent (e.g. an alcohol) and agglomerates or granules are built up of the moistened solids. Wet massing is continued until a desired homogenous particle size has been achieved whereupon the granulated product is dried.

An alternative to the "wet" granulation method is the "melt" granulation, which is also known as the "thermal plastic" granulation process, where a low melting solid is used as the granulation agent. Initially, the dry solids are blended and heated until the binder melts. As the binder is liquefied and spreads over the surface of the particles, the particles will adhere to each other and form granules. The binder solidifies upon cooling forming a dry granular product.

Wet granulation as well as melt granulation are energy intensive unit operations requiring complicated and expensive equipment as well as technical skill.

If the active ingredient, however, has suitable flow properties, then the granulation step can be avoided and tablets may be prepared by direct compression which is a cheaper production method.

The process used for the preparation of citalopram hydrobromide results in a product with a very small particle size around 2–20 μm that, as many other particulate products with a small particle size, has very poor flow properties. Thus, in order to achieve appropriate dosing of the citalopram hydrobromide during tabletting, it was considered necessary to make a granulate of citalopram hydrobromide with larger particle size and improved flow properties.

The citalopram tablet that is marketed is a tablet made from granulated citalopram hydrobromide with various excipients.

We have found that escitalopram has significantly different solubility and salt formation properties from the citalopram racemate. For example, the only pharmaceutically crystalline salt known so far is the oxalate, whereas the citalopram racemate forms crystalline hydrobromide and hydrochloride salts as well.

The escitalopram oxalate product prepared by crystallisation from acetone as outlined in U.S. Pat. No. 4,943,590 has, as the citalopram hydrobromide product described above, a very small particle size around 2–20 μm resulting in similarly poor flow properties.

In view of the fact that direct compression is much simpler and cheaper than the processes involving granulation there is a desire for larger crystals of escitalopram or pharmaceutical acceptable addition salts thereof.

Extensive laboratory and full-scale research has resulted in a new and inventive crystallisation process producing larger crystalline particles of escitalopram oxalate, i.e. particles of a size comparable to the size of the filler. Said particles are useful for the manufacture of directly compressed tablets. Accurate dosing in capsules may also be with such large particles.

OBJECTS OF THE INVENTION

It is the object of the present invention to provide large crystalline particles of escitalopram oxalate suitable for use in direct compression.

A second object of the invention is to provide a method for manufacture of large crystalline particles of escitalopram oxalate.

A third object of the invention is to provide a novel pharmaceutical unit dosage form containing large crystalline particles of escitalopram oxalate, wherein said unit dosage form may be a tablet, which preferably may be prepared by direct compression, or a capsule.

SUMMARY OF THE INVENTION

The invention then, inter alia, comprises the following alone or in combination:

Crystalline particles of escitalopram oxalate with a median particle size of at least 40 μm and suitable for use in a solid unit dosage form.

A method for the manufacture of crystalline particles of escitalopram oxalate having a median particle size of at least 40 μm and suitable for use in a solid unit dosage form wherein said method comprises that a solution of escitalopram oxalate in a suitable solvent system at a first temperature is gradually cooled down to a second temperature maintaining a controlled cooling profile and seeding the crystallisation batch by addition of crystals of escitalopram oxalate at least once during the cooling and followed by a holding time at said second temperature whereupon said crystals are isolated by conventional solid/liquid separation techniques.

A solid unit dosage form comprising escitalopram prepared by direct compression of a mixture of escitalopram base or a pharmaceutically acceptable salt thereof and pharmaceutically acceptable excipients, or by filling of said mixture in a hard gelatine capsule.

The direct compression of escitalopram, a filler and other pharmaceutically acceptable excipients into tablets has the great advantage, that the granulation and a drying step is avoided. Further, as the granulation step is avoided, it is no longer necessary to add a binding agent.

As used herein, "escitalopram oxalate" means any addition salt consisting of escitalopram, oxalic acid and optionally water. Examples of such salts are the hydrogen oxalate salt of escitalopram, i.e. the salt consisting of one molecule of escitalopram per molecule of oxalic acid, as well as the oxalate salt of escitalopram, i.e. the salt consisting of two molecules of escitalopram per molecule of oxalic acid.

As used herein, "crystalline particles" means any combination of single crystals, aggregates and agglomerates.

As used herein, "direct compression" means that the solid unit dosage form is prepared by compression of a simple mixture of the active ingredient and excipients, without the active ingredient having been subjected to an intermediate granulation process in order to embed it in a larger particle and improve its fluidity properties.

As used herein, "binder" means an agent, which is used in wet or melt granulation processes and acts as a binder in the granulated product.

As used herein, "particle size distribution" means the cumulative volume size distribution of equivalent spherical diameters as determined by laser diffraction at 1 bar dispersive pressure in a Sympatec Helos equipment. "Median particle size", correspondingly, means the median of said particle size distribution.

As used herein, "refluxing temperature" means the temperature at which the solvent or solvent system refluxes or boils at atmospheric pressure.

As used herein, "cooling profile" means the temperature of the crystallisation batch as a function of time.

As used herein, "cooling rate" means the decrease in temperature per time unit.

Thus in one embodiment of the present invention the crystalline particles of escitalopram oxalate have a median particle size of at least 40 μm, preferably in the range of 50–200 μm.

Flow, segregation and demixing properties and, hence, the suitability of the escitalopram oxalate crystals for direct compression depend, besides the median particle size, on the particle side distribution.

In another embodiment of the present invention crystalline particles of escitalopram oxalate having a median particle size of at least 40 μm, preferably in the range of 50–200 μm, and suitable for use in a solid unit dosage form are crystallised from a solution of escitalopram oxalate in a suitable solvent system. Said solvent system may comprise one or more alcohols and optionally water, preferably the solvent system is ethanol. Escitalopram oxalate is preferably dissolved in the solvent system at a temperature in the range between 50° C. and the refluxing temperature of the solvent system, preferably between 60° C. and the refluxing temperature and more preferred between 70° C. and the refluxing temperature, suitably the escitalopram oxalate is dissolved at the refluxing temperature. The amounts of pharmaceutically acceptable salt of escitalopram and solvent used are preferably corresponding to a solvent:solute weight ratio in the range of 0.05:1 to 0.6:1, more preferred 0.1:1 to 0.5:1 and most preferred 0.2:1 to 0.4:1. The solution of escitalopram oxalate is gradually cooled down to the temperature, at which the crystals will be isolated from the mother liquor, in the range of 0–20° C., preferably 0–15° C., and more preferred 7–15° C. maintaining a controlled cooling profile so that the cooling rate in an initial cooling period does not exceed 0.6° C./min, and preferably the cooling rate is kept within the range of 0.2–0.4° C./min, and said initial cooling period extends until the temperature of the crystallisation batch is below 60° C., preferably below 50° C. and more preferred below 40° C., suitably the cooling rate may be kept in this range for the entire cooling. The crystallisation batch is seeded by addition of crystals of escitalopram oxalate at least once during the cooling time in order to avoid excessive supersaturation with respect to escitalopram oxalate and resulting spontaneous crystallisation into small crystalline particles. The seeding is preferably repeated in order to ensure constant presence of crystalline escitalopram oxalate during the cooling, suitably the crystallisation batch is seeded semicontinuosly until crystallisation has started. The crystallisation batch is kept at said second temperature for a holding time for crystal growth for at least 1 hour, preferably in the range of 4 to 24 hours and more preferred 6 to 12 hours. After said holding time, the crystalline particles of escitalopram are isolated from the mother liquor using conventional separation techniques, e.g. filtration.

In one embodiment of the invention, the present invention relates to a tablet prepared from a mixture of large crystalline particles of escitalopram oxalate with a median particle size of at least 40 μm, preferably in the range of 50–200 μm and pharmaceutically acceptable excipients. Preferably the tablet is prepared by direct compression.

In another embodiment, the present invention relates to a capsule prepared by filling a mixture of large crystalline particles of escitalopram oxalate with a median particle size of at least 40 μm, preferably in the range of 50–200 μm and pharmaceutically acceptable excipients in a hard gelatine capsule.

Preferably, the solid unit dosage forms according to the invention do not contain a binder.

The solid unit dosage form according to the invention may contain 1–60% w/w active ingredient calculated as escitalopram base, preferably 4–40% w/w active ingredient calculated as escitalopram base, and more preferred 6–10% w/w active ingredient calculated as escitalopram base. Suitably, the solid unit dosage form of the invention contains 8% w/w active ingredient calculated as escitalopram base.

The solid unit dosage form according to the invention may contain a filler selected from lactose, or other sugars e.g. sorbitol, mannitol, dextrose and sucrose, calcium phosphates (dibasic, tribasic, hydrous and anhydrous), starch, modified starches, microcrystalline cellulose, calcium sulphate and/or calcium carbonate. In a preferred embodiment, the solid unit dosage form of the invention does not contain lactose.

Suitably the filler is a microcrystalline cellulose such as ProSolv SMCC90 manufactured by Penwest Pharmaceuticals or Avicel PH 200 manufactured by FMC Corporation.

Besides the active ingredient and filler, the solid pharmaceutical unit dosage forms may include various other conventional excipients such as disintegrants and optionally minor amounts of lubricants, colorants and sweeteners.

Lubricants used according to the invention may suitably be one or more selected from the group comprising metallic stearates (magnesium, calcium, sodium), stearic acid, wax, hydrogenated vegetable oil, talc and colloidal silica.

Preferably the lubricant is one or more selected from the group comprising talc, magnesium stearate or calcium stearate. Suitably the lubricant is a combination of talc and magnesium stearate. The weight percent of magnesium stearate in the solid unit dosage form is preferably in the range of 0.4% to 2%, and more preferred in the range of 0.7% to 1.4%.

Disintegrants include sodium starch glycolate, croscarmellose, crospovidone, low substituted hydroxypropylcellulose, modified cornstarch, pregelatinized starch and natural starch. Suitably the disintegrant is crosscarmellose such Ac-Di-Sol manufactured by FMC.

Optionally the solid, pharmaceutical unit dosage form of the invention may be coated. Suitably the coating is a film coating based on conventional coating mixtures such as Opadry OY-S-28849, white manufactured by Colorcon.

The solid, pharmaceutical unit dosage form of the invention may be prepared by conventional methods using a tablet press with forced feed capability.

The filled, hard gelatine capsule of the invention may be prepared by conventional methods using a capsule filler suitable for powder filling.

In the following, the invention is illustrated by way of examples. However, the examples are merely intended to illustrate the invention and should not be construed as limiting.

EXAMPLE 1

A wet filter cake obtained by precipitation of crude escitalopram oxalate by mixing of ethanolic solutions of escitalopram and oxalic acid, respectively, and containing approximately 35 kg escitalopram oxalate was suspended in 322 L ethanol. The material was dissolved by heating to reflux, and 150 L ethanol was removed by distillation. Cooling was applied, and the mixture was cooled from reflux to 15° C. with a cooling rate between 0.2 and 0.5° C./min in the temperature interval 80 to 40° C. During cooling, the mixture was seeded with escitalopram oxalate at 75, 65 and 60° C. (10 g each time). The crystallisation mixture was kept at 15° C. for 10 hours before the crystalline escitalopram oxalate was isolated. Purified escitalopram oxalate (27.7 kg, 58,2% of theory) was obtained by filtration of the crystallisation mixture, washing with ethanol and drying of the filter cake. Particle size distribution for the resulting escitalopram oxalate is listed in table 1.

TABLE 1

Particle size distribution (Sympatec Helos) for escitalopram oxalate crystals and ProSolv SCMC90

| Quantile (%) | Example 1 ($\mu$m) | ProSolv SCMC90 ($\mu$m) |
| --- | --- | --- |
| 90 | 455 | 291 |
| 50 | 163 | 130 |
| 10 | 13 | 37 |

EXAMPLE 2

Tablet prepared by direct compression of large crystalline particles of escitalopram oxalate.

Tablet ingredients:

Tablet core

| Escitalopram oxalate | 2554 g | (10.2% w/w) |
| Talc | 1400 g | (5.6% w/w) |
| ProSolv SMCC90 | 19896 g | (79.6% w/w) |
| Ac-Di-Sol | 900 g | (3.6%) |
| Magnesium stearate | 250 g | (1.0% w/w) |

Film coating

| Opadry OY-S-28849, white | 625 g | (2.5% w/w of core weight) |

Crystalline particles of escitalopram oxalate from example 1 and talc were sieved through 710 $\mu$m screen and blended at 6 rpm for 15 min in a 100 liter Bohle PTM 200 mixer. ProSolv SMCC90 and Ac-Di-Sol were added and blending continued for 15 min. Magnesium stearate was sieved through 710 $\mu$m screen and added and blending continued for 3 min.

25 kg of the resulting mixture was tabletted (125.000 tablets/hour) on a Korsch PH 230 tablet press fitted with oblong, embossed, scored 5,5×8 mm punches. Tablet core weight was set to 125 mg. The nominal yield was 200.000 tablets. The tablet press was run until the mixture level was just above the forced feeder, i.e. the tabletting was continued as long as possible in order to identify possible segregation tendencies in the last quantities of mixture. The tablets produced had satisfactory technical properties.

What is claimed is:

1. Crystalline particles of escitalopram oxalate having a median particle size of at least 40 $\mu$m.

2. The crystalline particles of claim 1 wherein the median particle size is from 50–200 $\mu$m.

3. A method for the manufacture of crystalline particles of escitalopram oxalate, which comprises (a) dissolving escitalopram oxalate in a solvent at a first temperature between about 50° C. and the refluxing temperature of the solvent to form a solution of escitalopram oxalate;

(b) gradually cooling the solution of escitalopram oxalate to a second temperature between about 0° C. and 20° C. while maintaining a controlled cooling rate;

(c) adding crystals of escitalopram oxalate during the cooling of step (b);

(d) holding the solution at the second temperature; and (e) isolating crystalline particles of escitalopram oxalate from the solution.

4. The method of claim 3 wherein the median particle size of the crystalline particles is at least 40 μm.

5. The method of claim 3 wherein the median particle size of the crystalline particles is from 50–200 μm.

6. The method of claim 3 wherein the solvent contains at least one alcohol and optionally water.

7. The method of claim 6 wherein the solvent system contains ethanol.

8. The method of claim 3 wherein the solute:solvent weight ratio is between about 0.05:1 and 0.6:1.

9. The method of claim 3 wherein the solute:solvent weight ratio is between about 0.1:1 and 0.5:1.

10. The method of claim 3 wherein the solute:solvent weight ratio is between about 0.2:1 and 0.4:1.

11. The method of claim 3 wherein the first temperature is between about 60° C. and the refluxing temperature of the solvent.

12. The method of claim 3 wherein the first temperature is between about 70° C. and the refluxing temperature of the solvent.

13. The method of claim 3 wherein the second temperature is between about 0° C. and 15 20 C.

14. The method of claim 3 wherein the second temperature is between about 7° C. and 15° C.

15. The method of claim 3 wherein the controlled cooling rate comprises an initial cooling period during which the cooling rate does not exceed 0.6° C. per minute.

16. The method of claim 15 wherein the initial cooling period comprises the time between the start of the cooling period and the time at which the temperature is below 60° C.

17. The method of claim 15 wherein the initial cooling period comprises the time between the start of the cooling period and the time at which the temperature is below 50° C.

18. The method of claim 15 wherein the initial cooling period comprises the time between the start of the cooling period and the time at which the temperature is below 40° C.

19. The method of claim 15 wherein the cooling rate of the solution comprises from 0.2 to 0.4° C. per minute.

20. The method of claim 3 which comprises adding crystals of escitalopram oxalate at least two times during the cooling of step (b).

21. The method of claim 3 which comprises holding the solution at the second temperature for at least one hour.

22. The method of claim 3 which comprises holding the solution at the second temperature for 4 to 24 hours.

23. The method of claim 3, which comprises holding the solution at the second temperature for 6 to 12 hours.

24. The method of claim 3, wherein step (e) comprises isolating the crystalline particles of escitalopram oxalate by solid/liquid separation techniques.

25. The method of claim 24, wherein the solid/liquid separation techniques comprise filtration.

26. A solid unit dosage form comprising the crystalline particles of escitalopram oxalate of claim 1.

27. A solid unit dosage form comprising the crystalline particles of escitalopram oxalate of claim 2.

28. The solid unit dosage form of claim 26, which comprises a tablet prepared by direct compression of a mixture of escitalopram oxalate and pharmaceutically acceptable excipients.

29. The solid unit dosage form of claim 28, wherein the tablet is coated.

30. The solid unit dosage form of claim 26, which is prepared by filling a hard gelatin capsule with a mixture of escitalopram oxalate and pharmaceutically acceptable excipients.

31. The solid unit dosage form of claim 26, which does not contain a binder.

32. The solid unit dosage form of claim 26, which comprises 1–30% w/w active ingredient calculated as escitalopram base.

33. The solid unit dosage form of claim 26, which comprises 4–20% w/w active ingredient calculated as escitalopram base.

34. The solid unit dosage form of claim 26, which comprises 6–10% w/w active ingredient calculated as escitalopram base.

35. The solid unit dosage form of claim 26, which further comprises a filler selected from e group consisting of lactose, sugars, calcium phosphates, starch, modified starches, micro crystalline cellulose, calcium sulfate and calcium carbonate.

36. The solid unit dosage form of claim 35, wherein the filler comprises a sugar selected from the group consisting of sorbitol, mannitol, dextrose and sucrose.

37. The solid unit dosage form of claim 35, wherein the filler comprises a calcium phosphate selected from the group consisting of dibasic, tribasic, hydrous and anhydrous calcium phosphate.

38. The solid unit dosage form of claim 35, wherein the filler comprises microcrystalline cellulose.

39. The solid unit dosage form of claim 38, wherein the microcrystalline cellulose is selected from the group consisting of ProSolv SMCC90 and Avicel PH 200.

40. The solid unit dosage form of claim 26, further comprising a lubricant.

41. The solid unit dosage form of claim 40, wherein the lubricant comprises a member selected from the group consisting of metallic stearates, stearic acid, wax, hydrogenated vegetable oil, talc and colloidal silica.

42. The solid unit dosage form of claim 41, wherein the lubricant comprises a metallic stearate selected from the group consisting of magnesium, calcium and sodium stearate.

43. The solid unit dosage form of claim 41, wherein the lubricant comprises a member selected from the group consisting of talc, magnesium stearate and calcium stearate.

44. The solid unit dosage form of claim 41, wherein the lubricant comprises talc and magnesium stearate.

45. The solid unit dosage form of claim 44, wherein the magnesium stearate is present in a weight percent of 0.4% to 2%, calculated on the weight of the solid dosage form.

46. The solid unit dosage form of claim 44, wherein the magnesium stearate is present in a weight percent of 0.7% to 1.4%, calculated on the weight of the solid dosage form.

47. The solid unit dosage form of claim 26, which is substantially free of lactose.

* * * * *

UNITED STATES PATENT AND TRADEMARK OFFICE
CERTIFICATE OF CORRECTION

PATENT NO. : 6,916,941 B2
DATED : July 12, 2005
INVENTOR(S) : Troels V. Christensen et al.

It is certified that error appears in the above-identified patent and that said Letters Patent is hereby corrected as shown below:

Column 7,
Line 24, please delete "1520 C" and substitute -- 15º C -- therefor.

Column 8,
Line 20, please delete "from e group" and substitute -- from the group -- therefor.
Line 22, please delete "micro crystalline" and substitute -- microcrystalline -- therefor.

Signed and Sealed this

Thirtieth Day of August, 2005

JON W. DUDAS
*Director of the United States Patent and Trademark Office*